(12) United States Patent
Xu et al.

(10) Patent No.: US 11,981,630 B1
(45) Date of Patent: May 14, 2024

(54) ABIETANE TYPE DITERPENE COMPOUND, PREPARATION METHOD AND APPLICATION THEREOF

(71) Applicant: Hangzhou Normal University, Hangzhou (CN)

(72) Inventors: Mingfeng Xu, Hangzhou (CN); Xiaohong Deng, Hangzhou (CN); Jinfeng Liang, Hangzhou (CN); Yidi Chen, Hangzhou (CN); Jing Ren, Hangzhou (CN); Qin Zhu, Hangzhou (CN)

(73) Assignee: HANGZHOU NORMAL UNIVERSITY, Hangzhou (CN)

( * ) Notice: Subject to any disclaimer, the term of this patent is extended or adjusted under 35 U.S.C. 154(b) by 0 days.

(21) Appl. No.: 18/103,843

(22) Filed: Jan. 31, 2023

(30) Foreign Application Priority Data

Oct. 20, 2022 (CN) .......................... 202211288533.5

(51) Int. Cl.
*C07C 49/747* (2006.01)
*A61P 35/02* (2006.01)
*C07C 45/79* (2006.01)

(52) U.S. Cl.
CPC ............ *C07C 49/747* (2013.01); *A61P 35/02* (2018.01); *C07C 45/79* (2013.01); *C07C 2603/26* (2017.05)

(58) Field of Classification Search
CPC ... C07C 49/747; C07C 45/79; C07C 2603/26; A61P 35/02
See application file for complete search history.

(56) References Cited

FOREIGN PATENT DOCUMENTS

CN 113336634 A * 9/2021 .............. A61P 35/00

OTHER PUBLICATIONS

Guo, K.et al. "Diversified abietane family diterpenoids from the leaves of Leucosceptrum canum and their cytotoxic activity." Phytochemistry, 2019. vol. 157: 43-52. (Year: 2019).*

* cited by examiner

*Primary Examiner* — Jean P Cornet
*Assistant Examiner* — Chihyi Lee
(74) *Attorney, Agent, or Firm* — Rachel Pilloff; Sean Passino; Pilloff Passino & Cosenza LLP

(57) ABSTRACT

Disclosed are an abietane type diterpene compound, a preparation method and an application thereof, relating to the technical field of anti-tumor compounds, where the compound has a chemical structure as shown in the following formula I:

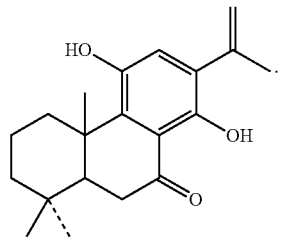

*Leucosceptrum canum* is extracted to prepare the abietane type diterpene compound according to the present application, and the prepared compound is effectively applied in inhibiting human lung cancer cell A549 and human myeloid leukemia cell HL-60.

5 Claims, 1 Drawing Sheet

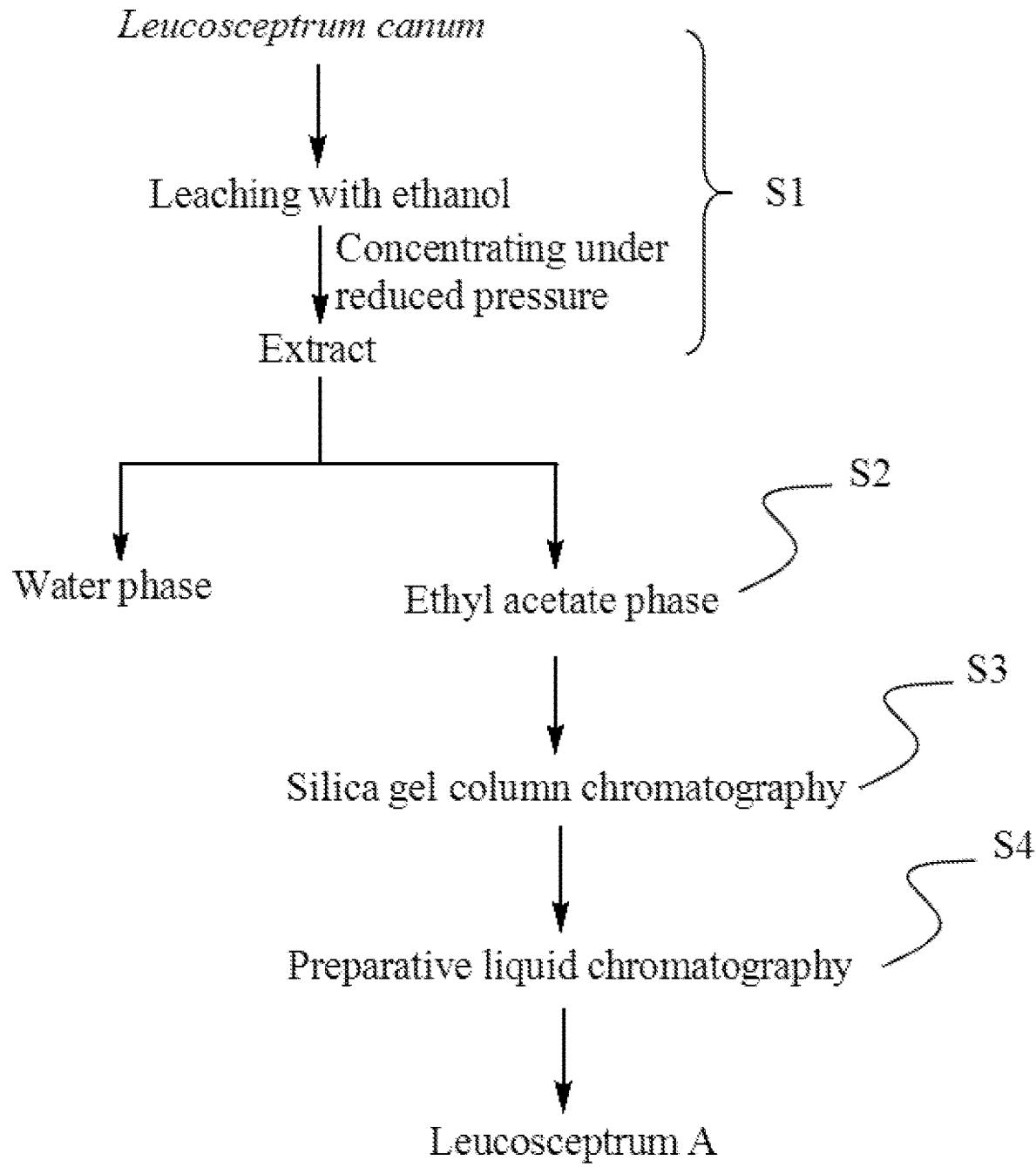

ABIETANE TYPE DITERPENE COMPOUND, PREPARATION METHOD AND APPLICATION THEREOF

CROSS-REFERENCE TO RELATED APPLICATIONS

This application claims priority to Chinese Patent Application No. 202211288533.5, filed on Oct. 20, 2022, the contents of which are hereby incorporated by reference.

TECHNICAL FIELD

The present application relates to the technical field of anti-tumor compounds, and in particular to an abietane type diterpene compound, a preparation method and an application thereof.

BACKGROUND

*Leucosceptrum canum* is leaves of the honey plant *Leucosceptrum canum* Smith belonging to the family Labiatae; the plant has efficacies of cleaning heat and detoxifying, relieving dampness and swelling, and stopping bleeding, and has been found in Sichuan and Yunnan of China.

It has been reported that the abietane type diterpene compound has already been used in pharmacology, examples can be found in the Chinese patent with publication number of CN101633660A, which discloses a new abietane type diterpene compound lushanrubescensin D and its preparation method and application, in addition to the physicochemical properties, optical activity of lushanrubescensin D, and the in vitro activity is screened by 3-(4,5)-dimethylthiahiazo (-z-yl)-3,5-di-phenytetrazoliumromide (MTT) assay, and the results show a significant inhibitory effect on mouse sarcoma cells and mouse liver cancer cells, making the compound possible to serve as a starter compound to develop new anti-tumor drugs, as well as for developing drugs of treating various clinically common and multifocal cancers.

The technical scheme described above provides an abietane type diterpene compound extracted from *Rabdosia rubescens* for preparing anti-tumor drugs. Currently, more than 60 chemical components, including diterpenoids, sesterterprnoids, flavonoids, phenylethanol glycosides, acyl glycosides and phenols, have been isolated from plants of the genus *Leucosceptrum*, among which diterpenoids and sesterterprnoids are the main types of structures; however, study on the anti-tumor activity of the chemical components from *Leucosceptrum* has not yet been reported.

SUMMARY

In view of this, the present application provides an abietane type diterpene compound, its preparation method and application; the abietane type diterpene compound is extracted and prepared from *Leucosceptrum canum*, and the compound has an inhibitory effect on human lung cancer cells and human promyelocytic leukemia cells.

The objectives of the present application are achieved by technical schemes as follows:

one aspect of the present application provides an abietane type diterpene compound *Leucosceptrum* A, with a chemical name of 11,14-dihydroxy-8,11,13,15-abietatetraen-7-one, and a structure is shown in the following formula I:

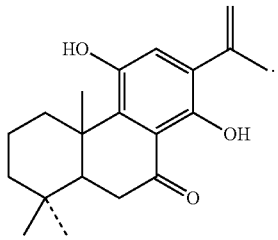

(I)

Another aspect of the present application provides a preparation method of the abietane type diterpene compound, including:

S1, taking air-dried *Leucosceptrum canum* as raw materials, crushing, leaching with organic solvents, and concentrating under a reduced pressure at low temperature to obtain extract;

S2, mixing the extract with water to obtain suspension, adding ethyl acetate for extraction, and concentrating under reduced pressure at a low temperature to obtain ethyl acetate extracting phase;

S3, separating the ethyl acetate extracting phase by silica gel column chromatography, and performing gradient elution with petroleum ether-ethyl acetate as eluent, where the petroleum ether and the ethyl acetate are in a volume ratio of 9.8-10.2:1, 4.8-5.2:1, and 2.8-3.2:1; collecting eluent corresponding to the volume ratio of petroleum ether to ethyl acetate of 2.8-3.2:1, followed by thin-layer chromatographic analysis and combining similar fractions to obtain initial components; and S4, separating the initial components by preparative liquid chromatography, and performing isocratic elution by using acetonitrile and water as an eluant to obtain the abietane type diterpene compound *Leucosceptrum* A as shown in the formula I.

Optionally, the organic solvent in the S1 is ethanol with a volume fraction of more that 90 percent (%), and the ethanol is in a volume-mass ratio of 10-20 milligrams (mL):1 gram (g) to the air-dried *Leucosceptrum canum*; the leaching is carried out under temperature of 65-75 degree Celsius (° C.) for 2-3 times, each time 4-6 hours (h).

Optionally, concentrating under reduced pressure at a low temperature in both the S1 and the S2 is carried out under a temperature of 40-50° C. with a vacuum degree of 0.07-0.09 Megapascal (MPa).

Optionally, the extract and water in the S2 are mixed in a mass ratio of 1:1-3, the ethyl acetate is in a volume ratio of 0.8-1:1 to the suspension, and the extraction is carried out for 2-4 times.

Optionally, the eluent in the S4 includes 40-50% by volume of acetonitrile, and water for a rest.

The abietane type diterpene compound *Leucosceptrum* A of the present application is extracted and purified by crushing, extracting, concentrating under reduced pressure, and separating various times using air-dried *Leucosceptrum canum* as a raw material; for the preparation, air-dried *Leucosceptrum canum* is used to facilitate the crushing; the eluent with an equal volume of petroleum ether and ethyl acetate is used as a separation system, where elution of single concentration fails to prepare the abietane type diterpene compound *Leucosceptrum* A since *Leucosceptrum canum* contains many impurities; moreover, gradient elution with unreasonable concentration arrangement, either too high or too low, leads to insufficient elution of the abietane type diterpene compound *Leucosceptrum* A. In the absence of reference material providing indications for the extraction of the abietane type diterpene compound *Leucosceptrum* A, there is a high degree of uncertainty in treating *Leucosceptrum canum* and obtaining *Leucosceptrum* A from them.

One aspect of the present application provides an application of the abietane type diterpene compound in preparing anti-tumor drugs.

Optionally, the anti-tumor drugs are applied in inhibiting tumor cells of human lung cancer cell A549 and human promyelocytic leukemia cell HL-60.

The application has the following beneficial effects:

the abietane type diterpene compound *Leucosceptrum* A of the present application is a natural antitumor compound extracted from *Leucosceptrum canum*; it is effective in inhibiting tumor cells, including human lung cancer cells A549 cells and human promyelocytic leukemia cells HL-60, especially in inhibiting human promyelocytic leukemia cells HL-60; the compound shows a strong antitumor activity and has a very promising application in preparing antitumor drugs, and plays an important role in enhancing the medical and economic value of *Leucosceptrum canum*.

BRIEF DESCRIPTION OF THE DRAWINGS

FIG. 1 shows a process of preparing an abietane type diterpene compound *Leucosceptrum* A.

DETAILED DESCRIPTION OF THE EMBODIMENTS

The present application is hereinafter described in detail in conjunction with the embodiments and the enclosed drawing.

Unless otherwise specified, the materials used in the present application are commercially available or commonly used in the art, and the methods in the following embodiments are conventional in the art if not specified.

Embodiment 1 Physical and chemical properties test of abietane type diterpene compound *Leucosceptrum* A 1.1 Determination of Molecular Structural Formula The Nuclear Magnetic Resonance (NMR) instrument used is a Bruker AVANCE III 500 NMR instrument manufactured by the Bruker Corporation, and the NMR is performed using the reagent of deuterated $CDCl_3$ (deuterated chloroform); the hydrogen spectrum and carbon spectrum data of the abietane type diterpene compound *Leucosceptrum* A is shown in Table 1 below.

TABLE 1

| | $^1$H-NMR (500 megahertz (MHz)) and $^{13}$C-NMR (125 MHz) data of Leucosceptrum A | |
|---|---|---|
| S/N | $\delta_H$ | $\delta_C$ |
| 1 | 1.08, m, α | 36.6, $CH_2$ |
| | 1.94, m, β | |
| 2 | 1.71, m, α | 19.4, $CH_2$ |
| | 1.51, m, β | |
| 3 | 2.22, dd (14.0, 6.5), α | 41.3, $CH_2$ |
| | 1.67, m, β | |
| 4 | — | 33.1, qC |
| 5 | 1.96, d (14.0) | 49.6, CH |

TABLE 1-continued

| | $^1$H-NMR (500 megahertz (MHz)) and $^{13}$C-NMR (125 MHz) data of Leucosceptrum A | |
|---|---|---|
| S/N | $\delta_H$ | $\delta_C$ |
| 6 | 2.74, m, α | 36.1, $CH_2$ |
| | 2.72, m, β | |
| 7 | — | 205.8, qC |
| 8 | — | 115.9, qC |
| 9 | — | 137.8, qC |
| 10 | — | 40.2, qC |
| 11 | — | 144.3, qC |
| 12 | 6.6, s | 124.4, CH |
| 13 | — | 119.2, qC |
| 14 | — | 155.7, qC |
| 15 | — | 143.1, qC |
| 16 | 5.33, br s | 111.2, $CH_2$ |
| | 5.02, br s | |
| 17 | 2.10, s | 22.0, $CH_3$ |
| 18 | 1.24, s | 32.9, $CH_3$ |
| 19 | 1.06, s | 21.6, $CH_3$ |
| 20 | 1.25, s | 18.0, $CH_3$ |

Note:
δ stands for a chemical shift; s represents a singlet peak; br s represents a broad singlet peak; m represents multiplet; and dd stands for double of doubles.

1.2 Molecular Weight Test

The compound is determined in terms of exact molecular weight by high-resolution mass spectrometry HR-ESI-MS, and HIR-ESI-MS [M-H]$^-$ is 313.1804; as determined from the NMR data and mass spectrometry data in Table 1, the abietane type diterpene compound *Leucosceptrum* A has a molecular formula of $C_{20}H_{26}O_3$, a molecular weight of 314, an unsaturation of 8, and a chemical name of 11,14-dihydroxy-8,11,13,15-abietatetraen-7-one with the structure shown in formula I.

1.3 Melting Point Test

The melting point is tested by WRS-1C melting point apparatus produced by Shanghai Instrument Physical Optics Instrument Co., Ltd., and it is tested that the melting point of the abietane type diterpene compound *Leucosceptrum* A is 245-246 degree Celsius (° C.).

Embodiment 2

An abietane type diterpene compound *Leucosceptrum* A is prepared in the present embodiment; and according to FIG. 1, the compound *Leucosceptrum* A is prepared as follows:

S1, air-drying and crushing 5 kilograms (kg) of *Leucosceptrum canum*, leaching with ethanol with volume percent of 95%, where the ethanol is added in a mass-volume ratio of *Leucosceptrum canum* to ethanol of 1 g:10 milliliters (mL), and the leaching is carried out under temperature of 70° C. for 3 times, each time for 5 hours (h); filtering off insoluble substances, combining filtrates, and then evaporating to dryness at a low temperature and under reduced pressure at a vacuum degree of 0.08 Megapascal (MPa) and a temperature of 45° C. to obtain extract;

S2, uniformly mixing the obtained extract with water according to a mass ratio of 1:2 to prepare a suspension, extracting with an equal volume of ethyl acetate for 3 times, combining extracted solutions, and evaporating to dryness at a low temperature and under the reduced pressure at a vacuum of 0.08 MPa and a temperature of 45° C. to obtain an ethyl acetate extract phase;

S3, evenly mixing the obtained ethyl acetate extract phase with silica gel of a same mass, then placing in a silica gel column for chromatography, and subjecting to gradient elution with petroleum ether-ethyl acetate as the eluent, where the petroleum ether is in volume ratios of 10:1, 5:1, and 3:1 respectively to the ethyl acetate in each gradient; collecting eluent corresponding to the volume ratio of petroleum ether to ethyl acetate of 3:1, followed by thin-layer chromatographic analysis and combining similar fractions to obtain initial components; and S4, separating the obtained initial components by preparative liquid chromatography, and performing isocratic elution by using acetonitrile and water in a volume ratio of 45:55 as the eluant to obtain the abietane type diterpene compound *Leucosceptrum* A of 16.0 milligrams (mg) with anti-tumor effect as shown in the formula I.

Embodiment 3

The present embodiment prepares an abietane type diterpene compound *Leucosceptrum* A according to the following steps:

S1, air-drying and crushing 5 kg of *Leucosceptrum canum*, leaching with ethanol with volume percent of 90%, where the ethanol is added in a mass-volume ratio of *Leucosceptrum canum* to ethanol of 1 g: 20 mL, and the leaching is carried out under temperature of 65° C. for 3 times, each time for 4 h; filtering off insoluble substances, combining filtrates, and then evaporating to dryness at a low temperature and under the reduced pressure at a vacuum degree of 0.07 MPa and a temperature of 50° C. to obtain extract;

S2, uniformly mixing the obtained extract with water according to a mass ratio of 1:1 to prepare a suspension, extracting with equal volume of ethyl acetate for 4 times, combining extracted solutions, and evaporating to dryness at a low temperature and under reduced pressure at a vacuum of 0.07 MPa and a temperature of 50° C. to obtain an ethyl acetate extract phase;

S3, evenly mixing the obtained ethyl acetate extract phase with silica gel of a same mass, then placing in a silica gel column for chromatography, and subjecting to gradient elution with petroleum ether-ethyl acetate as the eluent, where the petroleum ether is in volume ratios of 9.8:1, 4.8:1, and 2.8:1 respectively to the ethyl acetate in each gradient; collecting eluent corresponding to the volume ratio of petroleum ether to ethyl acetate of 2.8:1, followed by thin-layer chromatographic analysis and combining similar fractions to obtain initial components; and S4, separating the obtained initial components by preparative liquid chromatography, and performing isocratic elution by using acetonitrile and water in a volume ratio of 40:60 as the eluant to obtain the abietane type diterpene compound *Leucosceptrum* A of 11.4 mg with anti-tumor effect as shown in the formula I.

Embodiment 4

The present embodiment prepares an abietane type diterpene compound *Leucosceptrum* A according to the following steps:

S1, air-drying and crushing 5 kg of *Leucosceptrum canum*, leaching with the ethanol with volume percent of 95%, where the ethanol is added in a mass-volume ratio of *Leucosceptrum canum* to ethanol of 1 g:15 mL, and the leaching is carried out under temperature of 75° C. for 2 times, each time for 4 h; filtering off insoluble substances, combining filtrates, and then evaporating to dryness at a low temperature and under the reduced pressure at a vacuum degree of 0.09 MPa and a temperature of 40° C. to obtain extract;

S2, uniformly mixing the obtained extract with water according to a mass ratio of 1:1 to prepare a suspension, extracting with equal volume of ethyl acetate for 4 times, combining extracted solutions, and evaporating to dryness at a low temperature and under reduced pressure at a vacuum of 0.07 MPa and a temperature of 50° C. to obtain an ethyl acetate extract phase;

S3, evenly mixing the obtained ethyl acetate extract phase with the silica gel of a same mass, then placing in a silica gel column for chromatography, and subjecting to gradient elution with petroleum ether-ethyl acetate as the eluent, where the petroleum ether is in volume ratios of 10.2:1, 5.2:1, and 3.2:1 respectively to the ethyl acetate in each gradient; collecting eluent corresponding to the volume ratio of petroleum ether to ethyl acetate of 3.2:1, followed by thin-layer chromatographic analysis and combining similar fractions to obtain initial components; and S4, separating the obtained initial components by preparative liquid chromatography, and performing isocratic elution by using acetonitrile and water in a volume ratio of 50:50 as the eluant to obtain the abietane type diterpene compound *Leucosceptrum* A of 8.1 mg with anti-tumor effects as shown in the formula I.

Embodiment 5 Anti-tumor performance test of abietane type diterpene compound *Leucosceptrum* A The abietane type diterpene compound *Leucosceptrum* A prepared in Embodiment 2 is tested for its anti-tumor ability, with a process as follows:

in vitro tumor cell proliferation inhibition assay: exponential phase tumor cells are taken and the cell suspension concentration is adjusted (50,000-100,000 cells/mL), then the cell suspension is inoculated in 96-well plate with 100 microlitres (u L) per well (M L/well), followed by drug administration (100 μL/well) 24 h after inoculation; a blank control group, a cell control group and 6 drug groups with concentrations (3.12, 6.25, 12.5, 25, 50, 100 micromoles per litre (u mol/L)) are set up respectively, and the drug in the cell control group is cisplatin; after continuous cultivation for 72 h, 100 μL 3-(4,5)-dimethylthiahiazo(-z-yl)-3,5-diphenytetrazoliumromide (MTT) (1 mg/mL MTT dissolved in dulbecco's modified eagle medium (DMEM) culture solution) is added to each well, incubated at 37° C. for 4 h, then 150 μL acidified isopropyl alcohol (containing 0.04 mol/L HCl) is added to each well, and kept under darkness for 30 minutes (min); then the absorbance is measured at 570 nanometers (nm) by enzyme-labeled instrument, the inhibition rate of the tested drug on the proliferation of tumor cells and the half inhibition concentration ($IC_{50}$) of the tested substance on the proliferation of tumor cells (72 h) are calculated respectively; three parallels tests are arranged so as to reduce the influence of experimental errors, and the results are as follows.

5.1 Human Promyelocytic Leukemia Cell HIL-60

(1) Tables 2, 3 and 4 illustrate the inhibitory effect of cisplatin on HIL-60 cells in the control group.

TABLE 2

Inhibitory effect of parallel test I of cisplatin on HL-60 cells

| S/N | Blank | HL-60 cell quality control | Cisplatin concentrations (μmol/L) | | | | | |
|---|---|---|---|---|---|---|---|---|
| | | | 3.12 | 6.25 | 12.5 | 25 | 50 | 100 |
| 1 | −0.001 | 0.654 | 0.529 | 0.471 | 0.346 | 0.299 | 0.043 | 0.018 |
| 2 | 0.001 | 0.629 | 0.635 | 0.385 | 0.244 | 0.208 | 0.104 | 0.019 |
| 3 | 0.006 | 0.619 | 0.673 | 0.392 | 0.346 | 0.325 | 0.183 | 0.027 |
| Average | 0.002 | 0.634 | 0.6123 | 0.416 | 0.312 | 0.2773 | 0.11 | 0.0213 |
| Mean squared error | 0.0036 | 0.018 | 0.0746 | 0.0478 | 0.0589 | 0.0614 | 0.0702 | 0.0049 |
| Survival | | | 96.57% | 65.51% | 49.05% | 43.57% | 17.09% | 3.06% |

According to Graphpad Prism 6.0, $IC_{50}=14.36$.

TABLE 3

Inhibitory effect of parallel test II of cisplatin on HL-60 cells

| S/N | Blank | HL-60 cell quality control | Cisplatin concentrations (μmol/L) | | | | | |
|---|---|---|---|---|---|---|---|---|
| | | | 3.12 | 6.25 | 12.5 | 25 | 50 | 100 |
| 1 | −0.001 | 0.515 | 0.435 | 0.215 | 0.185 | 0.109 | 0.095 | 0.033 |
| 2 | 0 | 0.502 | 0.465 | 0.365 | 0.299 | 0.121 | 0.056 | 0.011 |
| 3 | −0.002 | 0.467 | 0.399 | 0.327 | 0.22 | 0.106 | 0.077 | 0.032 |
| Average | −0.001 | 0.4947 | 0.433 | 0.3023 | 0.2347 | 0.112 | 0.076 | 0.0253 |
| Mean squared error | 0.001 | 0.0248 | 0.033 | 0.078 | 0.0584 | 0.0079 | 0.0195 | 0.0124 |
| Survival | | | 87.56% | 61.20% | 47.55% | 22.80% | 15.53% | 5.31% |

According to Graphpad Prism 6.0, $IC_{50}=10.69$.

TABLE 4

Inhibitory effect of parallel test III of cisplatin on HL-60 cells

| S/N | Blank | HL-60 cell quality control | Cisplatin concentrations (μmol/L) | | | | | |
|---|---|---|---|---|---|---|---|---|
| | | | 3.12 | 6.25 | 12.5 | 25 | 50 | 100 |
| 1 | −0.002 | 0.515 | 0.442 | 0.391 | 0.197 | 0.095 | 0.038 | 0.017 |
| 2 | 0 | 0.536 | 0.512 | 0.453 | 0.201 | 0.192 | 0.096 | 0.019 |
| 3 | 0 | 0.528 | 0.509 | 0.447 | 0.295 | 0.202 | 0.045 | 0.015 |
| Average | −7E−04 | 0.5263 | 0.4877 | 0.4303 | 0.231 | 0.163 | 0.0597 | 0.017 |
| Mean squared error | 0.0012 | 0.0106 | 0.0396 | 0.0342 | 0.0555 | 0.0591 | 0.0317 | 0.002 |
| Survival | | | 92.66% | 81.78% | 43.96% | 31.06% | 11.45% | 3.35% |

According to Graphpad Prism 6.0, $IC_{50}=13.16$.

$IC_{50}=12.74\pm1.87$ of cisplatin is obtained according to the above data.

(2) The inhibitory effect of compound *Leucosceptrum A* on BIL-60 cells is shown in Tables 5, 6 and 7.

TABLE 5

Inhibitory effect of parallel test I of compound Leucosceptrum A on HL-60 cells

| S/N | Blank | HL-60 cell quality control | Leucosceptrum A concentrations (μmol/L) | | | | | |
|---|---|---|---|---|---|---|---|---|
| | | | 3.12 | 6.25 | 12.5 | 25 | 50 | 100 |
| 1 | 0.001 | 0.556 | 0.431 | 0.353 | 0.164 | 0.065 | 0.049 | 0.035 |
| 2 | 0.002 | 0.541 | 0.425 | 0.366 | 0.241 | 0.104 | 0.054 | 0.021 |
| 3 | 0 | 0.536 | 0.487 | 0.386 | 0.258 | 0.097 | 0.053 | 0.035 |
| Average | 0.001 | 0.5443 | 0.4477 | 0.3683 | 0.221 | 0.0887 | 0.052 | 0.0303 |
| Mean squared error | 0.001 | 0.0104 | 0.0342 | 0.0166 | 0.0501 | 0.0208 | 0.0026 | 0.0081 |
| Survival | | | 82.21% | 67.61% | 40.49% | 16.13% | 9.39% | 5.40% |

According to Graphpad Prism 6.0, IC$_{50}$=9.58.

TABLE 6

Inhibitory effect of parallel test II of compound Leucosceptrum A on HL-60 cells

| S/N | Blank | HL-60 cell quality control | Leucosceptrum A concentrations (μmol/L) | | | | | |
|---|---|---|---|---|---|---|---|---|
| | | | 3.12 | 6.25 | 12.5 | 25 | 50 | 100 |
| 1 | 0.001 | 0.541 | 0.452 | 0.417 | 0.177 | 0.054 | 0.048 | 0.043 |
| 2 | 0 | 0.571 | 0.417 | 0.398 | 0.129 | 0.055 | 0.045 | 0.021 |
| 3 | 0.002 | 0.488 | 0.395 | 0.381 | 0.239 | 0.064 | 0.037 | 0.032 |
| Average | 0.001 | 0.5333 | 0.4213 | 0.3987 | 0.1817 | 0.0577 | 0.0433 | 0.032 |
| Mean squared error | 0.001 | 0.042 | 0.0287 | 0.018 | 0.0551 | 0.0055 | 0.0057 | 0.011 |
| | | Survival | 78.96% | 74.70% | 33.94% | 10.64% | 7.95% | 5.82% |

According to Graphpad Prism 6.0, IC$_{50}$=9.19.

TABLE 7

Inhibitory effect of parallel test III of compound Leucosceptrum A on HL-60 cells

| S/N | Blank | HL-60 cell quality control | Leucosceptrum A concentrations (μmol/L) | | | | | |
|---|---|---|---|---|---|---|---|---|
| | | | 3.12 | 6.25 | 12.5 | 25 | 50 | 100 |
| 1 | 0.001 | 0.577 | 0.369 | 0.352 | 0.201 | 0.082 | 0.053 | 0.026 |
| 2 | 0.003 | 0.568 | 0.365 | 0.348 | 0.33 | 0.068 | 0.053 | 0.049 |
| 3 | 0.004 | 0.564 | 0.408 | 0.392 | 0.312 | 0.057 | 0.038 | 0.042 |
| Average | 0.0027 | 0.5697 | 0.3807 | 0.364 | 0.281 | 0.069 | 0.048 | 0.039 |
| Mean squared error | 0.0015 | 0.0067 | 0.0238 | 0.0243 | 0.0699 | 0.0125 | 0.0087 | 0.0118 |
| | | Survival | 66.67% | 63.73% | 49.09% | 11.79% | 8.00% | 6.41% |

According to Graphpad Prism 6.0, IC$_{50}$=8.42.

IC$_{50}$=9.06±0.59 of *Leucosceptrum* A is obtained according to the above data.

5.2 Human Lung Cancer Cell A549

(1) The inhibitory effect of cisplatin on human lung cancer cell A549 is shown in Tables 8, 9 and 10.

TABLE 8

Inhibitory effect of parallel test I of cisplatin on A549 cells

| S/N | Blank | A549 cell quality control | Cisplatin concentrations (μmol/L) | | | | | |
|---|---|---|---|---|---|---|---|---|
| | | | 3.12 | 6.25 | 12.5 | 25 | 50 | 100 |
| 1 | 0.001 | 0.661 | 0.641 | 0.489 | 0.231 | 0.212 | 0.205 | 0.203 |
| 2 | 0.002 | 0.652 | 0.642 | 0.446 | 0.254 | 0.288 | 0.207 | 0.198 |
| 3 | 0 | 0.731 | 0.715 | 0.391 | 0.278 | 0.221 | 0.196 | 0.173 |
| Average | 0.001 | 0.6813 | 0.666 | 0.442 | 0.2543 | 0.2403 | 0.2027 | 0.1913 |
| Mean squared error | 0.001 | 0.0432 | 0.0424 | 0.0491 | 0.0235 | 0.0415 | 0.0059 | 0.0161 |
| | | Survival | 97.75% | 64.82% | 37.24% | 35.18% | 29.64% | 27.98% |

According to Graphpad Prism 6.0, $IC_{50}=14.62$.

TABLE 9

Inhibitory effect of parallel test II of cisplatin on A549 cells

| S/N | Blank | A549 cell quality control | Cisplatin concentrations (μmol/L) | | | | | |
|---|---|---|---|---|---|---|---|---|
| | | | 3.12 | 6.25 | 12.5 | 25 | 50 | 100 |
| 1 | 0 | 0.612 | 0.602 | 0.431 | 0.301 | 0.267 | 0.213 | 0.186 |
| 2 | 0.001 | 0.653 | 0.647 | 0.48 | 0.238 | 0.234 | 0.202 | 0.202 |
| 3 | 0.003 | 0.626 | 0.613 | 0.491 | 0.239 | 0.208 | 0.199 | 0.179 |
| Average | 0.0013 | 0.6303 | 0.6207 | 0.4673 | 0.2593 | 0.2363 | 0.2047 | 0.189 |
| Mean squared error | 0.0015 | 0.0208 | 0.0235 | 0.0319 | 0.0361 | 0.0296 | 0.0074 | 0.0118 |
| Survival | | | 98.46% | 74.09% | 41.02% | 37.36% | 32.33% | 29.84% |

According to Graphpad Prism 6.0, $IC_{50}=17.85$.

TABLE 10

Inhibitory effect of parallel test III of cisplatin on A549 cells

| S/N | Blank | A549 cell quality control | Cisplatin concentrations (μmol/L) | | | | | |
|---|---|---|---|---|---|---|---|---|
| | | | 3.12 | 6.25 | 12.5 | 25 | 50 | 100 |
| 1 | 0 | 0.71 | 0.693 | 0.485 | 0.262 | 0.243 | 0.201 | 0.146 |
| 2 | −0.001 | 0.725 | 0.686 | 0.433 | 0.242 | 0.217 | 0.219 | 0.209 |
| 3 | 0.002 | 0.665 | 0.655 | 0.469 | 0.292 | 0.283 | 0.257 | 0.252 |
| Average | 0.0003 | 0.7 | 0.678 | 0.4623 | 0.265 | 30.2477 | 0.2257 | 0.2023 |
| Mean squared error | 0.0015 | 0.0312 | 0.0202 | 0.0266 | 0.0252 | 0.0332 | 0.0286 | 0.0533 |
| Survival | | | 96.86% | 66.03% | 37.88% | 35.35% | 32.21% | 28.87% |

According to Graphpad Prism 6.0, $IC_{50}=15.38$.

According to the above data, the $IC_{50}$ of cisplatin is $IC_{50}=15.95\pm1.69$.

(2) The inhibitory effect of compound *Leucosceptrum* A on A549 cells is shown in Tables 11, 12 and 13.

TABLE 11

Inhibitory effect of parallel test I of compound Leucosceptrum A on A549 cells

| S/N | Blank | A549 cell quality control | Leucosceptrum A concentrations (μmol/L) | | | | | |
|---|---|---|---|---|---|---|---|---|
| | | | 3.12 | 6.25 | 12.5 | 25 | 50 | 100 |
| 1 | 0 | 0.843 | 0.811 | 0.828 | 0.635 | 0.184 | 0.085 | 0.078 |
| 2 | 0.002 | 0.835 | 0.824 | 0.791 | 0.663 | 0.175 | 0.074 | 0.067 |
| 3 | 0.001 | 0.814 | 0.81 | 0.728 | 0.602 | 0.189 | 0.085 | 0.085 |
| Average | 0.001 | 0.8307 | 0.815 | 0.7823 | 0.6333 | 0.1827 | 0.0813 | 0.0767 |
| Mean squared error | 0.001 | 0.015 | 0.0078 | 0.0506 | 0.0305 | 0.0071 | 0.0064 | 0.0091 |
| Survival | | | 98.11% | 94.17% | 76.22% | 21.90% | 9.68% | 9.12% |

According to Graphpad Prism 6.0, $IC_{50}=17.55$.

TABLE 12

Inhibitory effect of parallel test II of compound Leucosceptrum A on A549 cells

| S/N | Blank | A549 cell quality control | Leucosceptrum A concentrations (μmol/L) | | | | | |
|---|---|---|---|---|---|---|---|---|
| | | | 3.12 | 6.25 | 12.5 | 25 | 50 | 100 |
| 1 | 0.003 | 0.796 | 0.72 | 0.711 | 0.636 | 0.221 | 0.077 | 0.073 |
| 2 | 0.002 | 0.793 | 0.753 | 0.786 | 0.687 | 0.182 | 0.074 | 0.066 |
| 3 | 0.003 | 0.865 | 0.869 | 0.769 | 0.683 | 0.173 | 0.059 | 0.058 |

TABLE 12-continued

Inhibitory effect of parallel test II of compound Leucosceptrum A on A549 cells

| | A549 cell quality | | Leucosceptrum A concentrations (μmol/L) | | | | | |
|---|---|---|---|---|---|---|---|---|
| S/N | Blank | control | 3.12 | 6.25 | 12.5 | 25 | 50 | 100 |
| Average | 0.0027 | 0.818 | 0.7807 | 0.7553 | 0.6687 | 0.192 | 0.07 | 0.0657 |
| Mean squared error | 0.0006 | 0.0407 | 0.0783 | 0.0393 | 0.0284 | 0.0255 | 0.0096 | 0.0075 |
| | | Survival | 95.42% | 92.31% | 81.68% | 23.22% | 8.76% | 7.73% |

According to Graphpad Prism 6.0, $IC_{50}$=18.38.

TABLE 13

Inhibitory effect of parallel test III of compound Leucosceptrum A on A549 cells

| | A549 cell quality | | Leucosceptrum A concentrations (μmol/L) | | | | | |
|---|---|---|---|---|---|---|---|---|
| S/N | Blank | control | 3.12 | 6.25 | 12.5 | 25 | 50 | 100 |
| 1 | 0.001 | 0.826 | 0.767 | 0.822 | 0.6 | 0.188 | 0.071 | 0.067 |
| 2 | 0 | 0.867 | 0.845 | 0.77 | 0.587 | 0.191 | 0.079 | 0.067 |
| 3 | 0.002 | 0.866 | 0.827 | 0.791 | 0.583 | 0.207 | 0.088 | 0.073 |
| Average | 0.001 | 0.853 | 0.813 | 0.7943 | 0.59 | 0.1953 | 0.0793 | 0.069 |
| Mean squared error | 0.001 | 0.0234 | 0.0408 | 0.0262 | 0.0089 | 0.0102 | 0.0085 | 0.0035 |
| | | Survival | 95.31% | 93.11% | 69.13% | 22.81% | 9.19% | 7.98% |

According to Graphpad Prism 6.0, $IC_{50}$=16.62.

According to the above data, the $IC_{50}$ of *Leucosceptrum* A is $IC_{50}$=17.52±0.88.

5.3 The 72-hour $IC_{50}$ (mol/L) of *Leucosceptrum* A and cisplatin on two cancer cells is shown in Table 14.

TABLE 14

72-hour $IC_{50}$(μmol/L) of Leucosceptrum A and cisplatin on two cancer cells

| Tumor cells | HL-60 cells | A-549 cells |
|---|---|---|
| Cisplatin | 12.74 ± 1.87 | 15.95 ± 1.69 |
| Leucosceptrum A | 9.06 ± 0.59 | 17.52 ± 0.88 |

It can be seen from the above tables 5-7 and 11-13 that the compound Leucoceptrum A with different concentrations has inhibitory effects on human lung cancer cell A549 and human promyelocytic leukemia cell HL-60, and the $IC_{50}$ values of Leucosceptrum A after 72 h reach 17.52±0.88 and 9.06±0.59 μmol/L, respectively, indicating that Leucoceptum A has a strong inhibitory effect on the growth of the above two tumor cells; specifically, the $IC_{50}$ value of Leucoceptum A on HL-60 cells is lower than that of control group with cisplatin, which indicates that Leucoceptum A has a very significant inhibitory effect on HL-60 cells.

The above embodiments are only used to illustrate the technical scheme of the present application and not to limit it. Although the present application is described in detail with reference to the preferred embodiments, it should be understood by those of ordinary skill in the art that the technical scheme of the present application may be modified or replaced by the same without departing from the purpose and scope of the technical scheme of the present application, which shall be covered by the scope of the claims of the present application. The technology, shape and construction parts not described in detail in the present application are all prior art.

What is claimed is:

1. A preparation method of the abietane type diterpene compound of formula (I):

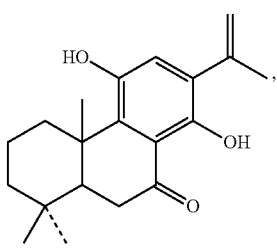

(I)

comprising:
S1, taking air-dried *Leucosceptrum canum* as raw materials, crushing, leaching with organic solvent, and concentrating under a reduced pressure at a low temperature to obtain an extract;
S2, mixing the extract with water to obtain a suspension, adding ethyl acetate for extraction, and concentrating under the reduced pressure at the low temperature to obtain an ethyl acetate extracting phase;
S3, separating the ethyl acetate extracting phase by silica gel column chromatography, and performing gradient elution with petroleum ether-ethyl acetate as an eluent, where the petroleum ether and the ethyl acetate are in a volume ratio of (9.8-10.2):1, (4.8-5.2):1, and (2.8-3.2):1; collecting the eluent corresponding to the volume ratio of petroleum ether to ethyl acetate of (2.8-3.2):1, followed by thin-layer chromatographic analysis and combining similar fractions to obtain initial components; and
S4, separating the initial components by preparative liquid chromatography, and performing isocratic elution by using acetonitrile and water as an eluant to obtain the abietane type diterpene compound.

2. The preparation method of the abietane type diterpene compound according to claim 1, wherein the ethanol in the S1 is in a volume-mass ratio of 10-20 milligrams (mL):1 gram (g) to the air-dried *Leucosceptrum canum*; and the leaching is carried out under temperature of 65-75 degree Celsius (° C.) for 2-3 times, each time with a duration of 4-6 hours (h).

3. The preparation method of the abietane type diterpene compound according to claim 1, wherein the concentrating under the reduced pressure at the low temperature in both the S1 and the S2 is carried out under a temperature of 40-50° C. with a vacuum degree of 0.07-0.09 Megapascal (MPa).

4. The preparation method of the abietane type diterpene compound according to claim 1, wherein the extract and water in the S2 are mixed in a mass ratio of 1:1-3, the ethyl acetate is in a volume ratio of 0.8-1:1 to the suspension, and the extraction is carried out for 2-4 times.

5. The preparation method of the abietane type diterpene compound according to claim 1, wherein the eluent in the S4 comprises 40-50% by volume of acetonitrile, and the rest is water.

\* \* \* \* \*